United States Patent [19]
Nuelle et al.

[11] Patent Number: 6,022,377
[45] Date of Patent: Feb. 8, 2000

[54] INSTRUMENT FOR EVALUATING BALANCE OF KNEE JOINT

[75] Inventors: Douglas G. Nuelle, Port Charlotte, Fla.; Mark B. Lester, Austin, Tex.; Mark E. Milburn, Georgetown, Tex.; Erroll Sweat, Austin, Tex.; Stuart Weikel, Fort Worth, Tex.

[73] Assignee: Sulzer Orthopedics Inc., Austin, Tex.

[21] Appl. No.: 09/009,070

[22] Filed: Jan. 20, 1998

[51] Int. Cl.[7] .................................................. A61B 17/56
[52] U.S. Cl. ............................. 623/20; 606/90; 606/102
[58] Field of Search .................. 623/20, 18; 606/79–86, 606/99, 102, 90

[56] References Cited

U.S. PATENT DOCUMENTS

| | | | |
|---|---|---|---|
| 5,417,693 | 5/1995 | Sowden et al. | 606/85 |
| 5,468,244 | 11/1995 | Attfield et al. | 606/90 |
| 5,540,696 | 7/1996 | Booth, Jr. et al. | 606/88 |
| 5,669,914 | 9/1997 | Eckhoff | 606/88 |
| 5,683,396 | 11/1997 | Tokish et al. | 606/87 |
| 5,735,904 | 4/1998 | Pappas | 623/20 |
| 5,800,438 | 9/1998 | Tuke et al. | 606/90 |

*Primary Examiner*—David H. Willse
*Assistant Examiner*—Suzette J. Jackson
*Attorney, Agent, or Firm*—Philip S. Lyren; Kenneth S. Barrow

[57] ABSTRACT

A knee joint balancing instrument. A first body includes a first paddle for engaging a proximal end of a tibial bone. A second body includes a second paddle for engaging a distal end of a femoral bone. A rack is attached to the first body and is moveable relative thereto in a superior-inferior direction. The second body is pivotally mounted to the rack for pivoting about an axis extending in an anterior-posterior direction. A ratchet is connected to the first body and to the rack for selectively restraining movement of the rack in the superior-inferior direction relative to the first body. A pinion is connected to the first body and engages the rack to cause movement of the rack in the superior-inferior direction relative to the first body. Tension can be induced in the medial and lateral soft tissues of the knee joint by moving the rack, the tension being evenly distributed between the medial and lateral condyles of the knee joint by the pivot mounting of the second paddle, such that an imbalanced response of the medial and lateral soft tissues to a balanced tensile load is indicated.

31 Claims, 6 Drawing Sheets

INSTRUMENT FOR EVALUATING BALANCE OF KNEE JOINT

BACKGROUND OF THE INVENTION

1. Field of the Invention

The present invention relates generally to surgical instruments used while implanting orthopedic joint prostheses, and relates more particularly to instruments that facilitate implantation of orthopedic knee joint prostheses.

2. Background Information

Implantable orthopedic prostheses, in one form, comprise man-made replacements for the ends and articulating surfaces of the bones of the skeleton. by Such prostheses are implanted to repair or reconstruct all or part of an articulating skeletal joint that is functioning abnormally due to disease, trauma, or congenital defect. The knee joint, as a major weight bearing joint, is known to degenerate relatively quickly in the event of abnormality. Also, the knee joint plays a critical role in ambulation and quality of life, resulting in great demand for surgical correction of abnormalities.

To facilitate their implantation, orthopedic knee prostheses have an associated set of specialized surgical instruments, including some that are useful only with a particular prosthesis design, and others that are more generally useful with different prostheses. In general, instruments are provided for cutting and shaping the distal end of the femur, the proximal end of the tibia, and, sometimes, the posterior side of the patella, to prepare those bones to receive prosthetic articulating surfaces. Instruments and jigs for guiding the aforementioned cutting and shaping operations are another important part of the instrument set. Other instruments are used for holding and placing the prosthesis components during surgery. Still another group of instruments is used in the course of surgery for measuring anatomical characteristics and evaluating the progress and accuracy of the surgical operations performed, prior to final implantation of the orthopedic prostheses. The use of such surgical instruments can be comprehended more readily with a basic understanding of knee joint anatomy and the principle knee prosthesis components, as discussed below.

The human knee joint involves three bones: the femur, the tibia and the patella, each having smooth articulation surfaces arranged for articulation on an adjacent articulation surface of at least one other bone. The femur includes at its distal extremity an articulation surface having medial and lateral convex condyles separated posteriorly by an intercondylar groove running generally in the anterior-posterior direction, the condyles joining at the distal-anterior face of the femur to form a patellar surface having a shallow vertical groove as an extension of the intercondylar groove. The patella includes on its posterior face an articulation surface having a vertical ridge separating medial and lateral convex facets, which facets articulate against the patellar surface of the femur and against the medial and lateral condyles during flexion of the knee joint, while the vertical ridge rides within the intercondylar groove to prevent lateral displacement of the patella during flexion. The tibia includes at its proximal end an articulation surface having medial and lateral meniscal condyles that articulate against the medial and lateral condyles, respectively, of the femur. The mutually engaging articulation surfaces of the femur and the patella together form, functionally, the patello-femoral joint, and the mutually engaging articulation surfaces of the femur and tibia together form, functionally, the tibio-femoral joint, which two functional joints together form the anatomical knee joint.

The femur and tibia that comprise the human knee joint are held in proper relationship to each other by soft tissues, i.e., non-bony tissues, that span the joint and are connected to the bones on each side of the joint. Primarily, the soft tissues that constrain and stabilize the knee joint are the ligaments, although the muscles and associated tendons that induce motion in the joint also play a role in stabilizing the joint. In order to preserve the proper relationship and spacing between the femur and tibia, it is important that the artificial articulating surfaces be located at approximately the same location as the natural articulating surfaces. Otherwise, the ligaments that stabilize the knee joint could be either too tight or too loose, or unbalanced between the medial and lateral sides of the joint, adversely affecting the kinematics of the knee, and leading to accelerated wear of the prosthesis.

All or part of one or more of the articulation surfaces of the knee joint may fail to perform properly, requiring the defective natural articulation surface to be replaced with a prosthetic articulation surface provided by an implantable prosthesis. To accommodate defects of varying scope, while permitting healthy portions of the knee joint to be conserved, a range of types of orthopedic knee implants is available. The range extends from total knee prosthesis systems for replacing the entire articulation surface of each of the femur, tibia and patella, to less comprehensive systems for replacing only the tibio-femoral joint, or only one side (medial or lateral) of the tibiofemoral joint, or only the patello-femoral joint. Commonly employed orthopedic knee prostheses include components that fall within one of three principle categories: femoral components, tibial components, and patellar components. A so-called "total" knee prosthesis includes components from each of these categories. The femoral component replaces the distal end and condylar articulating surfaces of the femur and may include a proximal stem that is received within the medullary canal at the distal end of the femur. The tibial component replaces the proximal end and meniscal articulating surfaces of the tibia and may include a distal stem that is received within the medullary canal at the proximal end of the tibia. The patellar component replaces the posterior side and natural articulating surface of the patella. Sometimes, the patellar component is not used, and the natural articulating surface of the patella is allowed to articulate against the femoral component.

The tibial component of a total knee prosthesis is configured to be received upon and fixed to the proximal end of the tibia. The tibia is prepared to receive the tibial component by resecting a portion of the proximal end of the tibia to leave a substantially horizontal planar bony plateau. Sometimes the exposed medullary canal at the proximal end of the tibia is also reamed to receive a stem portion of the tibial component. The tibial component typically includes a plate portion having an inferior planar surface conforming to the resected bony plateau at the proximal end of the femur. The plate portion may or may not include a depending stem or keel for receipt within a prepared tibial medullary canal. Commonly, a meniscal bearing insert is received atop the plate portion of the tibial component to provide an artificial meniscal articulating surface for receiving the condylar surfaces of the femoral component of the total hip prosthesis. The femoral condylar articulating surfaces articulate against the tibial meniscal articulating surface to restore motion to a defective knee joint.

One known type of tibial component involves a tibial plate made of a bio-compatible metal such as titanium or a titanium alloy, and a meniscal bearing insert made of a bio-compatible polymer such as ultra-high molecular weight polyethylene. The tibial plate is shaped generally as a flat plate having a perimeter that generally conforms to the transverse sectional perimeter of the resected proximal tibia. The tibial plate includes a planar distal, or inferior, surface for engaging the resected proximal tibia, and a proximal, or superior, surface for engaging and receiving the meniscal bearing insert. The bearing insert has an inferior surface that engages the superior surface of the plate portion, and may include locking tabs or other means for fixing the bearing insert to the plate portion against relative movement.

The femoral component of a total knee prosthesis is configured to be received upon and fixed to the distal end of the femur. The femur is prepared to receive the femoral component by resecting a portion of the distal end of the femur to remove the natural condylar articulating surfaces and leave a polygonal resected bone surface. The resected bone surface typically includes three to five intersecting planar surfaces that together form a generally convex, faceted distal surface that mates congruently with a similar concave, faceted proximal surface of the femoral component. Sometimes the exposed medullary canal at the distal end of the femur is also reamed to receive a stem portion of the femoral component. The femoral component typically includes a pair of smoothly curved, highly polished, artificial condylar articulating surfaces that replace the natural condyles of the femur. The condylar articulating surfaces are received upon and articulate against the artificial meniscal articulating surface of the meniscal bearing insert described above. Typically, the femoral component is made of a bio-compatible metal such as titanium, titanium alloy, or cobalt chrome alloy.

Various instrument designs have been proposed for tensioning the ligaments of the knee joint during surgery, by applying a spreading force between the tibia and femur, so that the spacing between the femur and tibia can be ascertained for a given amount of tension. Typically, the spacing/tension relationship is measured independently on both the medial and lateral sides of the joint, to detect any inequality between the medial and lateral soft-tissue ligaments. If one side of the knee joint is found to be more tightly constrained than the other, the tighter side will be released surgically to restore balance to the knee. One disadvantage of prior art instruments is that it is cumbersome to apply and maintain a fixed amount of spreading force to the knee joint, while allowing for detection of unbalance. This is because the spreading force is applied independently to the medial and lateral sides of the joint. It would be advantageous to provide an instrument that would allow a selected amount of spreading force to be applied to the knee joint as a whole, while automatically distributing the force evenly between the medial and lateral sides of the joint, and permitting any unbalance of the knee joint to be readily discerned. This and other desirable advantages are provided by the present invention described below.

SUMMARY OF THE INVENTION

According to one aspect of the present invention, a knee joint balancing instrument has a first body including a first paddle for engaging one of a proximal end of a tibial bone and a distal end of a femoral bone. A second body includes a second paddle for engaging the other of the proximal end of the tibial bone and the distal end of the femoral bone. A rack is attached to the first body and movable relative thereto in a superior-inferior direction. The second body is pivotally mounted to the rack for pivoting about an axis extending in the anterior-posterior direction. Ratchet means is connected to the first body and the rack for selectively restraining movement of the rack in the superior-inferior direction relative to the first body.

It is an object of the present invention to provide an instrument for use in connection with the implantation of orthopedic knee joint prosthesis, for evaluating the tensile balance of the soft tissues of the knee joint.

Other objects and advantages of the present invention will be apparent from the following descriptions of the preferred embodiment illustrated in the drawings.

DETAILED DESCRIPTION OF THE PREFERRED EMBODIMENT

Figure 1:
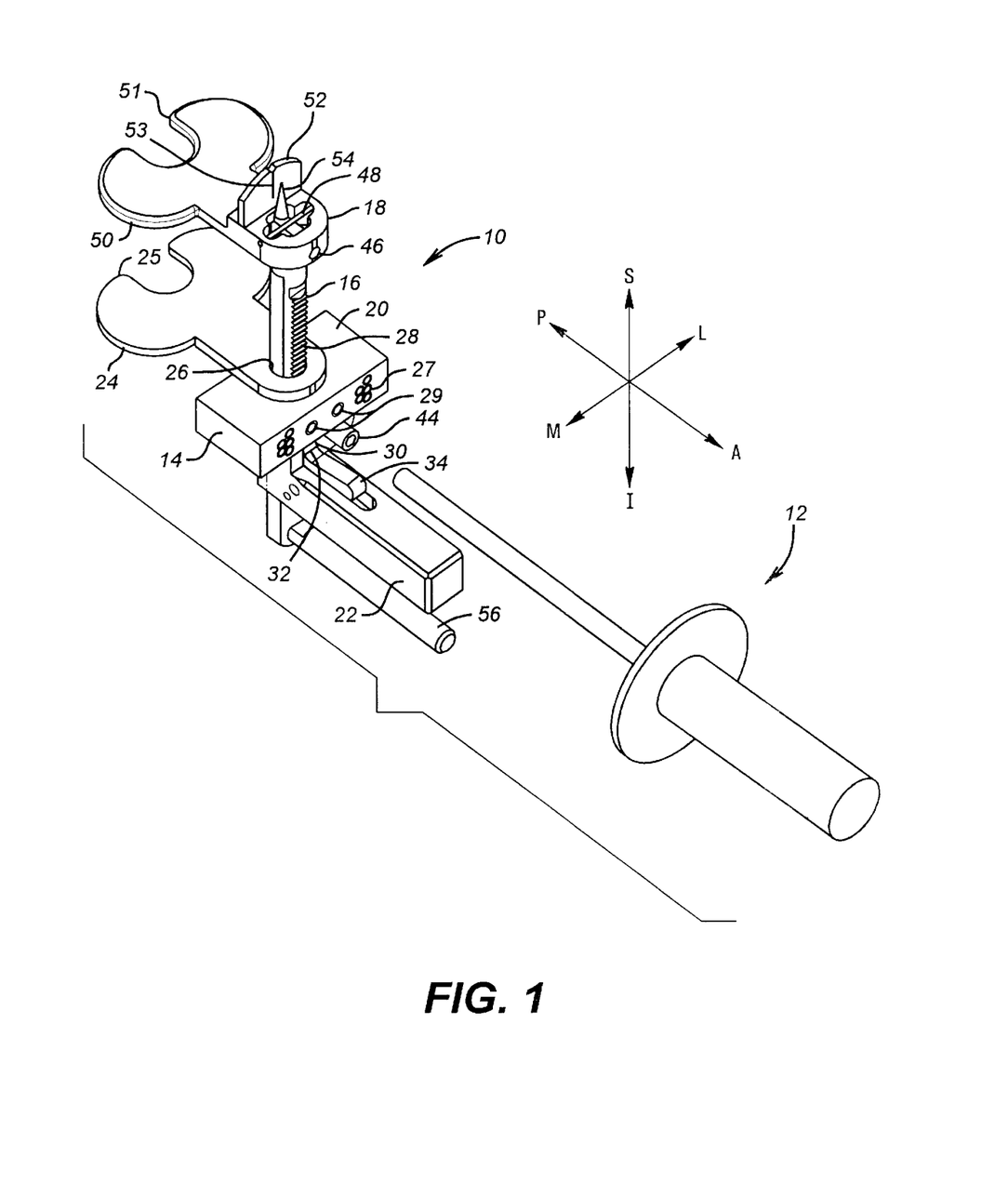
FIG. 1 is a perspective view of a knee balancing instrument useful in connection with the implantation of an orthopedic knee joint prosthesis, and a torque driver accessory instrument, constructed according to the present invention.
Figure 2:
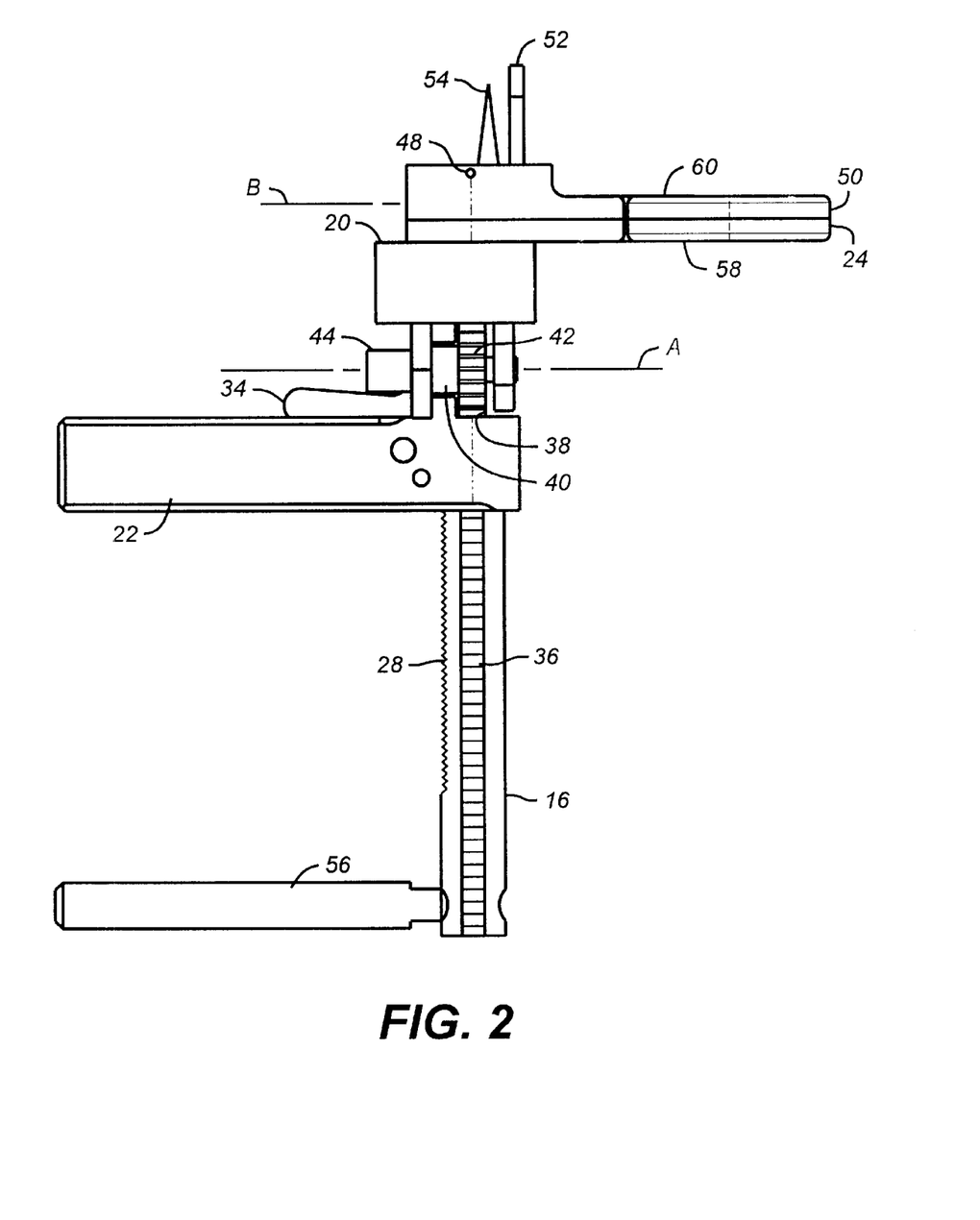
FIG. 2 is a right side elevation view of the knee balancing instrument of FIG. 1, shown in a first orientation.

Referring to FIGS. 1 and 2, a knee balancing instrument 10 is shown. A torque driver accessory instrument 12 is also shown in FIG. 1. A directional frame of reference is included in FIG. 1 to facilitate the following description of knee balancer 10 in terms of well-known anatomical directions as they would apply to knee balancer 10 in use. The anterior-posterior direction is indicated by the symbols A-P, the superior-inferior direction is indicated by the symbols S-1, and the medial-later direction is indicated by the symbols M-L. As shown in FIG. 1, the medial and lateral directions indicated by M and L, respectively, correspond to use of knee balancer 10 on the left knee. When used on the right knee, the M and L directions would be reversed.

Knee balancer 10 includes as principle components a first body 14, a rack 16, and a second body 18. First body 14 includes an attachment block 20, a handle 22 extending from the inferior end of block 20 generally in the anterior direction, and a first paddle 24 extending from the superior end of block 20 generally in the posterior direction and includes a posterior notch 25. As preferred, attachment block 20, handle 22 and first paddle 24 are integrally joined. A bore 26 extends through attachment block 20 in the superior—inferior direction and is open at the superior and inferior ends. A plurality of mounting pin holes 27 extend through attachment block 20 in the anterior-posterior direction to either side of bore 26, for receiving mounting pins (not shown) therethrough. The mounting pins can be driven into the anterior side of the tibia to attach block 20 to the tibia in a stable, but temporary, manner. Blind holes 29 are located on the anterior face of attachment block and extend in the anterior-posterior direction for receiving an extension member and an associated alignment rod, described further below. Rack 16 is disposed within bore 26 in sliding relationship for movement in the superior-inferior direction relative to attachment block 20. Ratchet teeth 28 are located along a substantial length of the anterior side of rack 16. A passage 30, open at the anterior side of attachment block 20, communicates with bore 26 and provides access to ratchet teeth 28 of rack 16. A pawl 32, pivotally attached to first body 14, extends through passage 30 and engages ratchet teeth 28 to restrain rack 16 against movement in the inferior direction when so engaged. A spring (not shown) biases pawl 32.toward engagement with ratchet teeth 28. Pawl 32 includes a release lever 34 which, when depressed in the inferior direction toward handle 22, causes pawl 32 to pivot out of engagement with ratchet teeth 28, allowing rack 16 to move in the inferior direction. Rack 16 includes rack gear teeth 36 extending along a substantial length of rack 16 on the right side of rack 16. A passage 38, open at the right side of attachment block 20, communicates with bore 26 and provides access to rack gear teeth 36 of rack 16. A pinion gear 40, mounted to first body 14 for rotation about an axis A extending in the anterior-posterior direction, includes pinion gear teeth 42 that extend through passage 38 and engage rack gear teeth 36. Pinion gear 40 includes a driving interface 44 exposed on the anterior side of first body 14 for receiving the torque driver 12 in rotary driving engagement. Torque driver 12 is used to rotate pinion gear 40 in the appropriate direction to move rack 16 in the superior-inferior direction relative to first body 14. Second body 18 is pivotally mounted to the superior end of rack 16 by pivot pin 46 for pivoting movement about an axis B extending in the anterior-posterior direction. A spring-rod 48, extending in the medial-lateral direction and r[]mounted at each end to second body 18, has a middle portion that can engage the superior end of rack 16. As second body 18 is pivoted on pivot pin 46, the middle portion of spring-rod 48 engages the superior end of rack 16 and is deflected elastically. The spring-rod 48 tends to bias second body 18 toward a neutral pivot orientation relative to rack 16. A second paddle 50, integral with second body 18 and extending generally in the posterior direction, lies parallel to first paddle 24 when second body 18 is in the neutral pivot orientation and includes a posterior notch 51. An angle reference plate 52, affixed to second body 18, has an index line 53 that extends in the superior direction when second body 18 is in the neutral pivot orientation. An indicator pin 54, affixed to rack 16, is offset anteriorly from angle reference plate 52 and extends in the superior direction, parallel to the longitudinal axis of rack 16. A rack handle 56, affixed to the inferior end of rack 16, extends generally in the anterior direction parallel to handle 22 of first body 14 to prevent rack 16 from escaping bore 26, and to facilitate manual movement of rack 16 relative to first body 14 when pawl 32 is disengaged from ratchet teeth 28.

Referring specifically to FIG. 2, knee balancer 10 is shown in a first orientation in which first paddle 24 and second paddle 50 are drawn together such that the spacing in the superior-inferior direction between the inferior surface 58 of first paddle 24 and the superior surface 60 of second paddle 50 is at a minimum. As preferred, the minimum spacing is about 9 mm.

Figure 3:
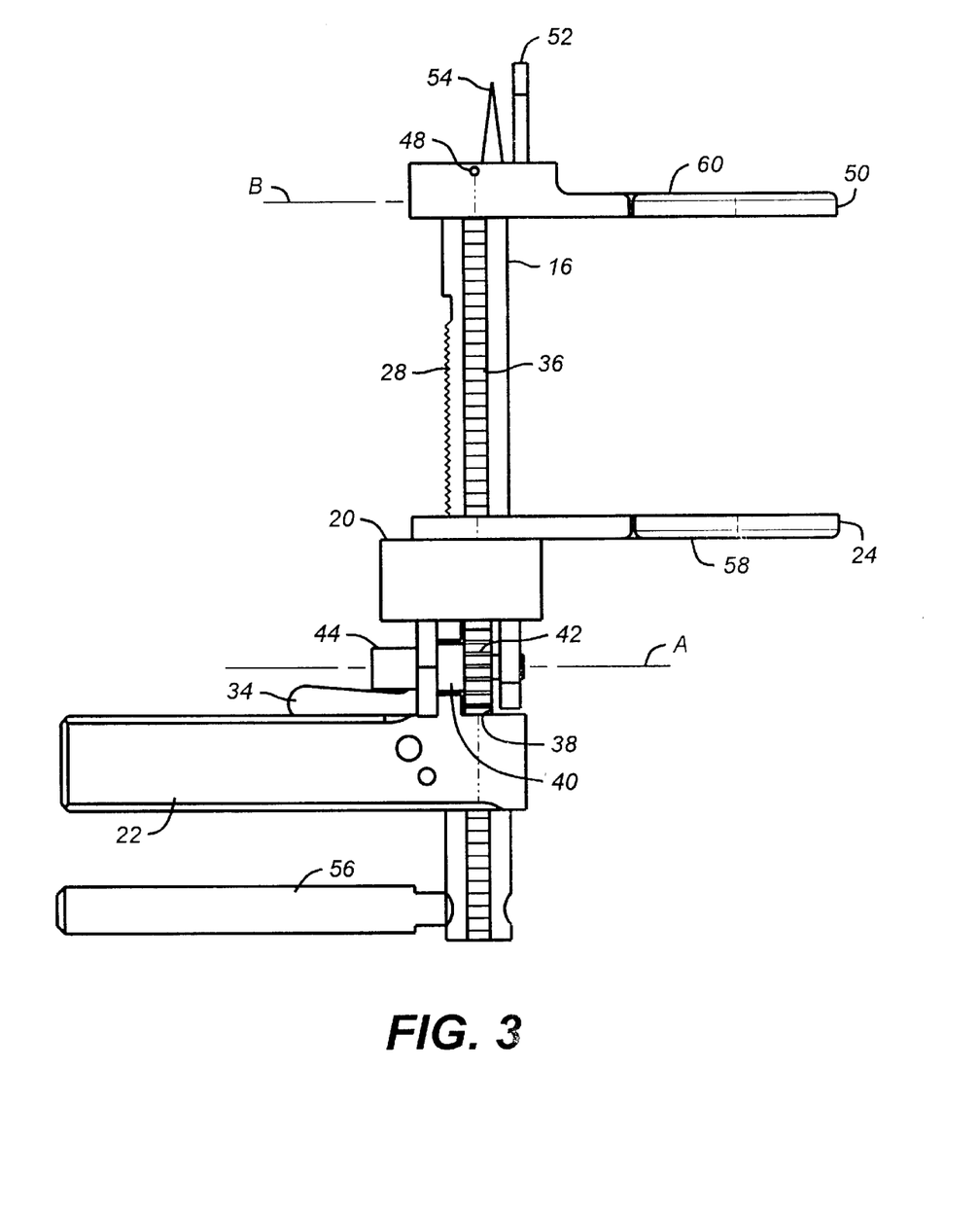
FIG. 3 is a right side elevation view of the knee balancing instrument of FIG. 1, shown in a second orientation.

Referring specifically to FIG. 3, knee balancer 10 is shown in a second orientation in which first paddle 24 and second paddle 50 are spaced apart such that the spacing in the superior-inferior direction between the inferior surface 58 of first paddle 24 and the superior surface 60 of second paddle 50 is at a maximum. As preferred, the maximum spacing is about 84 mm.

Figure 4:
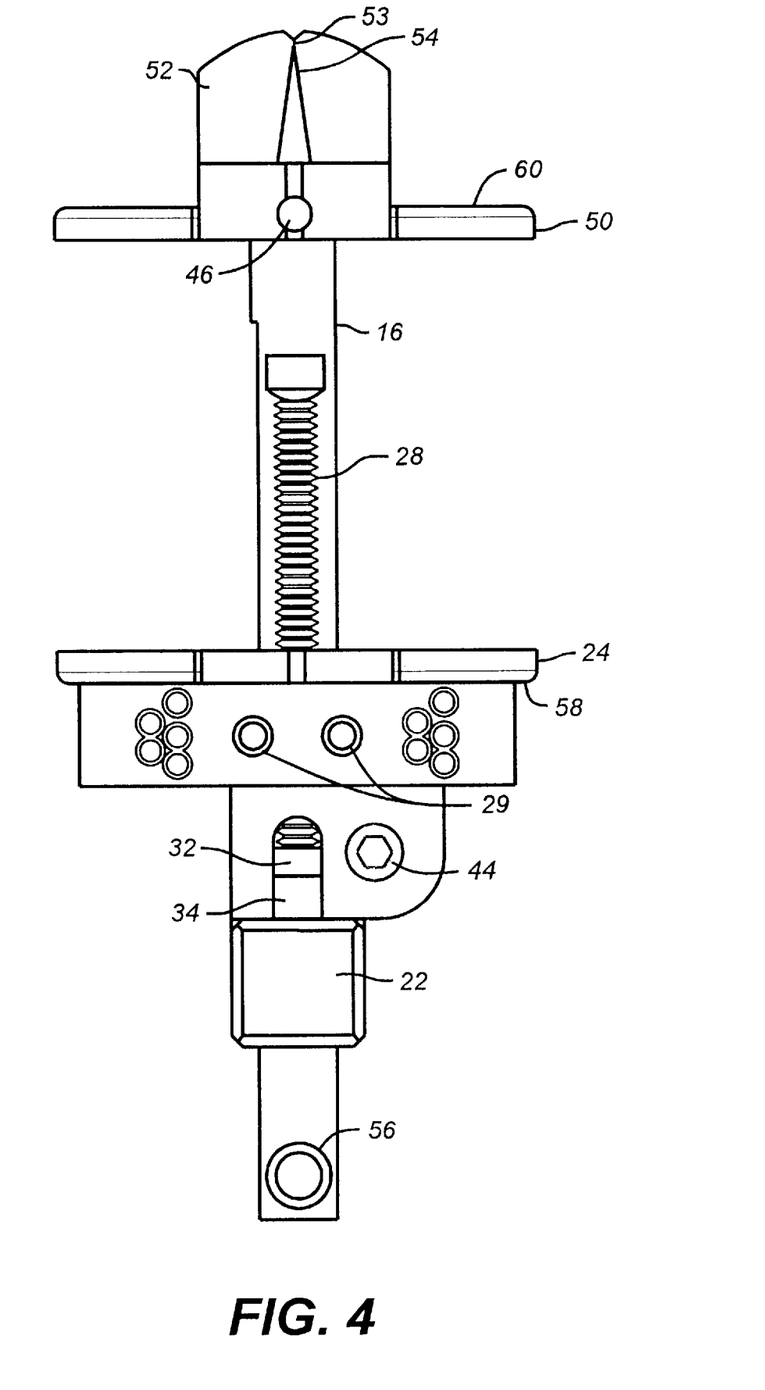
FIG. 4 is a rear elevation view of the knee balancing instrument of FIG. 1, shown in a balanced orientation.
Figure 5:
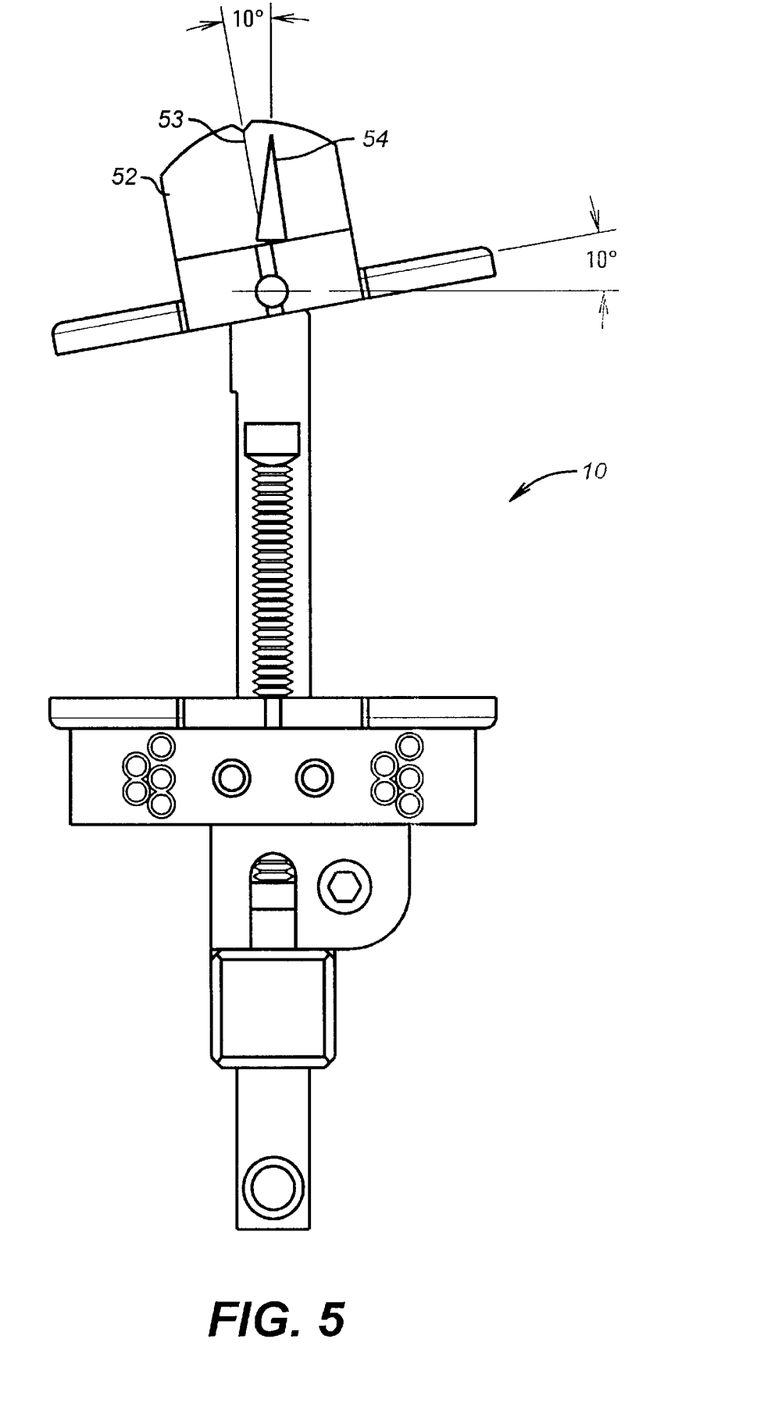
FIG. 5 is a rear elevation view of the knee balancing instrument of FIG. 1, shown in a first unbalanced orientation.
Figure 6:
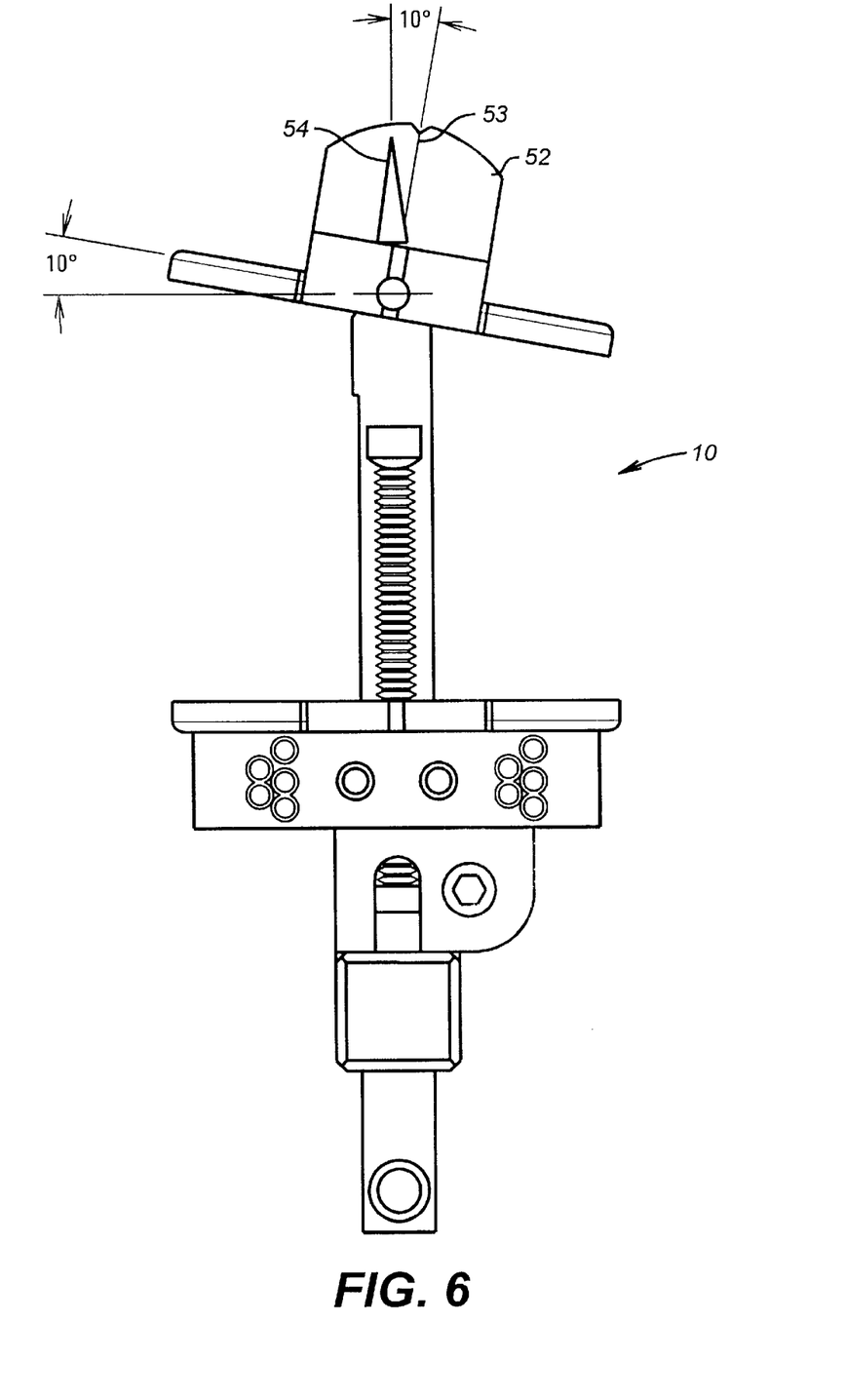
FIG. 6 is a rear elevation view of the knee balancing instrument of FIG. 1, shown in a second unbalanced orientation.

With reference to FIGS. 4, 5 and 6, second paddle 50 is shown in the neutral orientation, pivoted left about 10°, and pivoted right about 10°, respectively. As shown in FIGS. 5 and 6 especially, any deviation of second paddle 50 relative to the neutral position shown in FIG. 4 is discernable by the physician by observing the misalignment of index line 53 of angle reference plate 52 relative to indicator pin 54. The direction of tilt is readily observable.

As preferred, the knee balancer 10 described above is used to determine the state of balance of a knee joint under tension. Using knee balancer 10, a selected load is applied to the knee joint along the mechanical axis of the knee joint. The pivoted mounting of second paddle 50 provides even distribution of the load across the knee joint, such that any imbalance of soft tissue constraints can be detected. This results in a clear and accurate indication of the state of balance of the knee joint, and of the soft tissues that require release to achieve balance.

Once the tibia has been resected to the desired plane, the knee joint is placed in flexion. The knee balancer 10 is inserted into the knee joint such that the inferior surface 58 of the first paddle 24 rests on the resected bony plateau of the proximal tibia. As an option, first body 14 can be secured in place on the tibia by way of mounting pins received through mounting pin holes 27 and driven into the tibial bone. The second paddle 50 is moved in the superior direction, along with rack 16, relative to first paddle 24 and first body 14, until the superior surface 60 of second paddle 50 engages the distal condyles of the femur. The second paddle is then moved further in the superior direction by means of the torque driver 12 applied to pinion driving interface 44. The spacing between the first paddle 24 and second paddle 50 is increased, placing the soft tissues of the knee joint in tension, until the desired amount of tension is achieved, as indicated by the torque measured by the torque driver 12. The joint gap is then measured, and the balance of the knee is evaluated by observing the orientation of the index line 53 of angle reference plate 52 relative to the indicator pin 54. If the index line 53 of angle reference plate 52 and indicator pin 54 are aligned, then the soft tissue of the knee joint is balanced. If angle reference plate 52 is displaced at an angle to the left or right of indicator pin 54, then surgical release of the soft tissue on the side to which angle reference plate 52 is displaced will be necessary to restore balance to the knee joint. Surgical release is effected until balance is indicated by index line 53 of angle reference plate 52 becoming aligned with indicator pin 54. After soft tissue release, the joint tension should again be checked with the torque driver 12 and adjusted to the desired level, if necessary. The joint gap should then be measured again. Tension is then released by depressing the pawl handle 34, disengaging pawl 32 from ratchet teeth 28 and allowing second paddle 50 and rack 16 to move freely toward first paddle 24 and first body 14. The knee joint should then be placed in extension and the joint gap and balance should be checked again according to the steps described above. The joint gap should be the same in both flexion and extension. Once the joint gap and knee balance are determined to be satisfactory, the alignment of the knee joint should be checked. This is accomplished by mounting an extension member (not shown) to the anterior face of alignment block 20 such that the extension member extends in the anterior-posterior direction. An alignment-rod (not shown) extends superiorly and inferiorly from the extension member, 61 Pins of the extension member are received in a removable fit within holes 29 of alignment block 20. While the extension member and the alignment rod are so mounted, the surgeon observes whether the rod is aligned with the hip, knee and ankle joints, all three of which should be aligned for proper kinematics of the joints.

The present invention has been illustrated and described with particularity in terms of a preferred embodiment. Nevertheless, it should be understood that no limitation of the scope of the invention is intended thereby. The scope of the invention is defined by the claims appended hereto. It should also be understood that variations of the particular embodiments described herein incorporating the principles of the present invention will occur to those of ordinary skill in the art and yet be within the scope of the appended claims.

We claim:

1. A knee joint balancing instrument comprising:
   a rack;
   a first body movably mounted on the rack and including a first paddle for engaging one of a proximal end of a tibial bone and a distal end of a femoral bone;
   a second body pivotally mounted on the rack and including a second paddle for engaging the other of said proximalend of said tibial bone and said distal end of said femoral bone;
   means interconnecting said rack and said first body for moving the first paddle in a superior-inferior direction relative to the second paddle;
   means interconnecting said rack and said second body for pivoting said second paddle from a level position to a tilted position about an axis extending in an anterior-posterior direction;
   said second body being resiliently mounted to automatically return to the level position from the tilted position; and
   ratchet means connected to said first body and said rack for selectively restraining movement of said rack in the superior-inferior direction relative to said first body.

2. The knee joint balancing instrument of claim 1, in which said second paddle is anatomically shaped including a medial portion for engaging a medial condyle and a lateral portion for engaging a lateral condyle of said proximal end of said bone.

3. The knee joint balancing instrument of claim 2, in which said pivot axis is disposed intermediate said medial portion and said lateral portion of said paddle.

4. The knee joint balancing instrument of claim 3, in which said second paddle includes a posterior notch providing clearance for a posterior cruciate ligament.

5. The knee joint balancing instrument of claim 3, in which said first paddle is anatomically shaped including a medial portion for engaging a medial condyle and a lateral portion for engaging a lateral condyle of said proximal end of said bone.

6. The knee joint balancing instrument of claim 5, in which said first paddle includes a posterior notch providing clearance for a posterior cruciate ligament.

7. The knee joint balancing instrument of claim 1 wherein said means for moving said first paddle includes a pinion connected to said first body and engaging said rack.

8. The knee joint balancing instrument of claim 7, and further including torque driving means removably engagable with said pinion means.

9. The knee joint balancing instrument of claim 7, and further including indicator means connected to said first body and to said second body for indicating angular displacement of the knee joint.

10. The knee joint balancing instrument of claim 9, in which said second paddle includes a medial portion for engaging a medial condyle and a lateral portion for engaging a lateral condyle of said proximal end of said bone, said pivot axis being disposed intermediate said medial portion and said lateral portion of said paddle;

whereby tension can be induced in the medial and lateral soft tissues of the knee joint by moving said rack, said tension being evenly distributed between the medial and lateral condyles of the knee joint by said pivot mounting of said second paddle, such that an imbalanced response of the medial and lateral soft tissues to a balanced tensile load is indicated.

11. The knee joint balancing instrument as defined in claim 1 wherein the first body includes a first handle extending therefrom.

12. The knee joint balancing instrument as defined in claim 1 wherein the first body includes a bore formed therethrough for receiving the rack.

13. The knee joint balancing instrument as defined in claim 1 wherein the first body includes a plurality of mounting pin receiving holes formed therein.

14. The knee joint balancing instrument as defined in claim 1 wherein the first body includes alignment tool receiving bores formed thereon.

15. The knee joint balancing instrument as defined in claim 1 wherein said ratchet means includes ratchet teeth formed on said rack and a pawl pivotally attached to said first body.

16. The knee joint balancing instrument as defined in claim 7 wherein said rack includes rack gear teeth formed thereon for engaging said pinion.

17. The knee joint balancing instrument as defined in claim 11 wherein said body includes a resilient member engaging said rack for biasing said second body to the level position relative to said rack.

18. The knee joint balancing instrument as defined in claim 17 wherein said second body includes an angle reference member.

19. The knee joint balancing instrument as defined in claim 18 wherein said angle reference member includes an index thereon.

20. The knee joint balancing instrument as defined in claim 19 wherein said rack includes a second handle extending therefrom and an indicator member mounted thereon and extending adjacent the index.

21. An instrument for tensioning and balancing a knee joint comprising:
   a main support;
   a first member mounted on the main support and including a first paddle;
   a second member pivotally mounted on the main support and including a second paddle and an angle reference member thereon;
   a drive device interconnecting the first member and the main support for positionably adjusting the first member toward and away from the second member; and
   a spring rod interconnecting the second member and the main support for biasing the second paddle to a neutral position relative to the angle reference member.

22. The instrument as defined in claim 21 wherein the first member includes a first handle extending therefrom and the main support includes a second handle extending therefrom.

23. The instrument as defined in claim 21 wherein the first member includes mounting pin receiving holes formed therein.

24. The instrument as defined in claim 21 wherein the first member includes alignment tool receiving holes formed therein.

25. The instrument as defined in claim 21 wherein the main support includes ratchet teeth for engagement with a pawl mounted on the first member.

26. The instrument as defined in claim 21 wherein the drive device is a pinion mounted on the first member for engagement with the main support.

27. The instrument as defined in claim 21 wherein the main support includes an indicator member extending therefrom adjacent the angle reference member.

28. The instrument as defined in claim 26 wherein the main support includes rack gear teeth formed thereon for engaging said pinion.

29. The instrument as defined in claim 27 wherein said angle reference member includes an index thereon.

30. An instrument for tensioning and evaluating balance for a knee joint comprising:

a main support;

a first member adjustably mounted on the main support and including a first paddle extending in a lateral orientation relative to the main support;

a second member mounted on the main support and including a second paddle and an angle reference member thereon, the second paddle extending in lateral orientation relative to the main support substantially parallel to the first member and pivotally movable to an angular position from the lateral orientation;

a drive device interconnecting the first member and the main support for positionably adjusting the first member toward and away from the second member; and a spring rod interconnecting the second member and the main support for biasing the second paddle from the angular position to the lateral orientation.

31. The instrument as defined in claim 30 wherein the main support includes an indicator member extending from a first end thereof adjacent the angle reference member, and a handle extending from a second end thereof.

* * * * *